United States Patent

Winkelmann et al.

[11] 3,951,963
[45] Apr. 20, 1976

[54] 0-(SUBSTITUTED-AMINOALKYL)-5-NITROIMIDAZOLE-(2)-ALDOXIMES

[75] Inventors: Erhardt Winkelmann; Ulrich Gebert, both of Kelkheim, Taunus; Wolfgang Raether, Drieichenhain, all of Germany

[73] Assignee: Hoechst Aktiengesellschaft, Frankfurt am Main, Germany

[22] Filed: Mar. 5, 1974

[21] Appl. No.: 448,376

[30] Foreign Application Priority Data
Mar. 7, 1973 Germany.......................... 2311177

[52] U.S. Cl............................ 260/240 G; 260/309; 424/246; 424/248; 424/263; 424/267; 424/274
[51] Int. Cl.²............... C07D 401/12; C07D 403/12; C07D 413/12; C07D 233/32
[58] Field of Search............. 260/240 G, 240 A, 309

[56] References Cited
UNITED STATES PATENTS

| | | | |
|---|---|---|---|
| 3,060,177 | 10/1962 | Druey et al. | 260/240 G |
| 3,299,090 | 1/1967 | Hoff et al. | 260/309 |
| 3,634,447 | 1/1972 | Gastrock | 260/309 |
| 3,646,016 | 2/1972 | Henry et al. | 260/240 G |
| 3,660,385 | 5/1972 | Albrecht et al. | 260/240 A |
| 3,790,593 | 2/1974 | Carlson et al. | 260/309 |

*Primary Examiner*—Allen B. Curtis
*Attorney, Agent, or Firm*—Henry W. Koster

[57] ABSTRACT
Novel 0-(dialkylaminoalkyl)-1-alkyl-5-nitroimidazole-(2)-aldoximes are described as well as their manufacture and use for treating protozoal diseases. The novel compounds correspond to the general formula

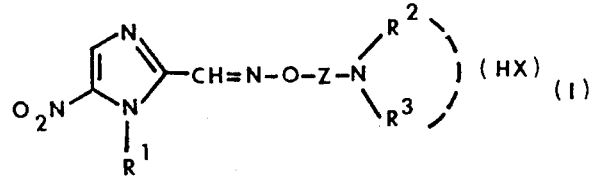

in which $R^1$ stand for a hydrogen atom, a methyl, ethyl or hydroxyethyl group, Z stands for a linear or branched alkylene chain of 2 to 3 carbon atoms, and $R^2$ and $R^3$ each stands for an identical or different lower alkyl radical having from 1 to 4 carbon atoms or the group $-NR^2R^3$ can be part of a saturated heterocyclic ring which may contain further substituents preferably a methyl group or/and hetero atoms, such as, especially the pyrrolidine, piperidine, morpholine, thiamorpholine, tetrahydro-1,4-thiazine-1,1-dioxide and piperazine ring, and HX can be a non-toxic, physiologically acceptable acid.

15 Claims, No Drawings

0-(SUBSTITUTED-AMINOALKYL)-5-NITROIMIDAZOLE-(2)-ALDOXIMES

The present invention relates to o-(dialkylaminoalkyl)-1-alkyl-5-nitroimidazole-(2)-aldoximes and to a process for their manufacture.

1-Alkyl-5-nitroimidazole-(2)-aldoximes and -aldoximalkyl ethers are disclosed in German Offenlegungsschrift No. 1,595,928 as being effective against protozoal diseases.

1-(2'-Hydroxyethyl)-2-methyl-5-nitro-imidazole (Metronidazol) is used for the treatment of protozoal diseases, for example, trichomoniasis and amoebiasis.

The present invention provides o-(dialkylaminoalkyl)-1-alkyl-5-nitroimidazole-(2)-aldoximes of the formula I

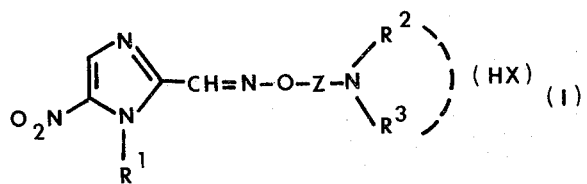

in which $R^1$ stands for a hydrogen atom, a methyl, ethyl or hydroxyethyl group, Z stands for a linear or branched alkylene chain of 2 to 3 carbon atoms and $R^2$ and $R^3$ each stand for an identical or different lower alkyl radical having from 1 to 4 carbon atoms, or the group -$NR^2R^3$ can be part of a saturated heterocyclic ring which may contain further substituents preferably a methyl group or/and hetero atoms, such as, especially the pyrrolidine, piperidine, morpholine, thiamorpholine, tetrahydro-1,4-thiazine-1,1-dioxide and piperazine ring, and HX can be a non-toxic, physiologically acceptable acid.

The compounds of the invention have a pronounced activity against trichomonads and amebae, which activity is superior to that of the 5-nitro-imidazoles mentioned above.

This invention also provides a process for the manufacture of o-(dialkylaminoalkyl)-1-alkyl-5-nitroimidazole-(2)-aldoximes of the formula I, which comprises reacting a) 1-alkyl-5-nitroimidazole-(2)-aldehydes of the formula II or the reactive derivatives thereof,

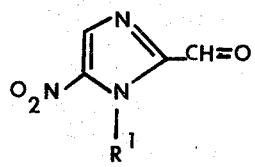

in which $R^1$ is defined as above, with o-substituted hydroxyl amines of the formula II or the salts thereof

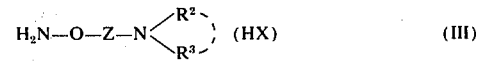

in which $R^2$ and $R^3$ and Z are defined as above, or b) 1-Alkyl-5-nitroimidazole-(2)-aldoximes of the formula IV

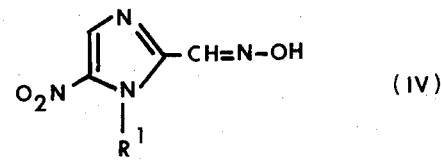

in which $R^1$ is defined as above, with halogenated alkyl amines of the formula V or the salts thereof

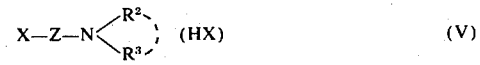

in which X stands for a halogen atom or an arylsulfonic acid ester grouping, in the presence of acid-binding agents and, optionally, converting them into their salts.

Suitable starting substances of the formula II are the following aldehydes or the derivatives thereof: 1-Methyl-5-nitro-imidazole(2)-aldehyde, 1-ethyl-5-nitroimidazole-(2)-aldehyde or 1-(2'-hydroxyethyl)-5-nitroimidazole-(2)-aldehyde as well as the mono- and diacetals, mono- and dimercaptals, and the mono- and diacetates thereof; also the correspondingly substituted aldimines, oximes, hydrazones, semi-carbazones, thiosemicarbazones and the corresponding aldehyde-cyanohydrins and bisulfite compounds.

Suitable compounds of the formula III are, for example, o-(2-Dimethylaminoethyl)-hydroxylamine, o-(2-dimethylaminoethyl)-hydroxylamine, o-(2-dipropylaminoethyl)-hydroxylamine, o-(2-isopropylaminoethyl)-hydroxylamine, o-(2-dibutylaminoethyl)-hydroxylamine, o-(2-diisobutylaminoethyl)-hydroxylamine, o-(2-pyrrolidinoethyl)-hydroxylamine, o-(2-piperidinoethyl)-hydroxylamine, o-(2-morpholinoethyl)-hydroxylamine, o-(N-methylpiperazinoethyl)-hydroxylamine and o-(2-dimethylamino-1-propyl)-hydroxylamine, the 2-dialkylamino-1-propyl-hydroxylamines corresponding to the aminoethyl-hydroxylamines mentioned above, as well as o-(3-dialkylamino-1-propyl)hydroxylamines which correspond to the aminoethyl-hydroxylamines mentioned above.

Suitable compounds of the formula IV are, for example, 1-methyl-, 1-ethyl-, 1-(2'-hydroxyethyl)-5-nitroimidazole-(2)-aldoximes.

Suitable compounds of the formula V are, for example, 2-dimethylaminoethyl chloride, 2-dimethylaminoethyl bromide, 2-dimethylaminoethyl-benzenesulfonic acid ester or -4'-toluenesulfonic acid ester and the corresponding 2-dimethylaminoethyl halides or esters, as well as the 2-dipropylaminoethyl-, 2-diisopropylaminoethyl-, 2-dibutylaminoethyl-, 2-diisobutylaminoethyl-, 2-pyrrolidinoethyl-, 2- piperidinoethyl-, 2-morpholinoethyl-, 2-N-methyl-piperazino derivatives. The corresponding 2-dialkylamino-1-propyl halides or esters as well as the corresponding 3-dimethylamino-1-propyl-halides or -benzenesulfonic acid esters or toluenesulfonic acid esters can also be used.

The reactions are advantageously carried out using equimolar amounts of reactants, and a solvent or dispersing agent, preferably an alcoholic solvent according to method a) and preferably a polar aprotic solvent according to method b). As alcohols, there may be used, for example, methanol, ethanol, propanol or isopropanol. As aprotic solvents, there may be used, for example, dimethyl formamide, dimethyl acetamide, N-methylpyrrolidone, tetramethyl urea, hexamethyl-phosphoric acid triamide, dimethyl sulfoxide. The reaction temperatures may be within the range of from 0° to 200°C, advantageously from 20° to 80°C in alcoholic solvents and from 100° to 150°C in aprotic solvents. Depending on the reaction conditions used, the reaction times are in the range of from a few minutes to several hours. The reaction products are obtained in the form of bases or they can be isolated by converting them into salts. As acids, there may be used, for example, hydrohalic acids, especially, hydrochloric acid, as well as sulfuric acid, phosphoric acid, tartaric acid, etc.

The o-(dialkylaminoalkyl)-1-alkyl-5-nitroimidazole-(2)-aldoximes of the invention are suitable for the treatment of protozoal diseases in mammals, for example, those diseases caused by infection with *Trichomonas vaginalis* and *Entamoeba histolytica*. The preparations may be in a form suitable for oral or local administration, and are preferably in unit dosage form, for example, tablets and capsules for oral administration, the daily doses being about 10 to 750 mg of the active substance in admixture with a conventional diluent and/or excipient. For local administration, the preparations may be in the form of jellies, creams, ointments or suppositories In addition to a good compatibility, the compounds of the invention are distinguished by a safe activity against trichomonads and amebae, which activity is generally superior to the known pharmaceutical compositions 1-methyl-5-nitroimidazole-(2)-aldoxime and Metronidazol, in vitro and in vivo as can be seen from the following Tables.

The following examples illustrate the invention:

EXAMPLE 1: (test for activity)

Activity against Trichomonas foetus was generally tested on home-bred albino mice (NMRI-strain) of both sexes. The body weight of each animal was from 10 to 12 g.

The substance to be tested was administered orally by means of an esophagal sound either in an aqueous solution, or, in the case of sparingly water-soluble compounds, in a Tylose suspension. The overall dosage was administered in two units, the first one two hours prior to infection and the second one two hours after infection. 5 Mice were used for each substance to be tested and for each dosage.

Infection was brought about by intraperitonael injection of 19 million infective agents per animal in a suspension in 0.5 ml of a culture medium, Merck I. The standard Metronidazol was administered by the same route and in the same dosage as the substance to be tested (see Table I).

As infection controls there were generally used 10 mice which, after infection, were not treated any more. Another 5 mice served as a zero control, that is to say, these animals were neither treated nor infected.

Six days after infection, all the test animals were killed and the peritoneal exudate was examined for trichomonads. Mice which had died before were subjected to the same examination.

The tested substance was judged on the concentration of infective agents to be found in the peritoneal exudate on the sixth day after infection. For this purpose, the concentration of infective agents established with the test composition was compared to that of the standard and of the infection control. The scheme, according to which the tested substance and the standard were judged with regard to the concentration of infectants established, was the following:

ineffective: Concentration of infective agents was not substantially reduced as compared to infection control. Judgement: 3; 4 effective:
 a. faint: Concentration of infective agents was moderately reduced compared with infection control. Judgement: 2
 b. unsatisfactory: Concentration of infective agents was substantially reduced compared with infection control. Judgement: 1
 c. no infective agents found. Judgement: 0

TABLE I

| composition | dosage in mg/kg mouse, per os | concentration of infectant Trichomonas foetus in 4 mice |
|---|---|---|
| I | 2 × 150 | 0 0 0 0 |
|   | 2 × 100 | 0 0 0 0 |
|   | 2 × 50  | 0 0 0 0 |
|   | 2 × 25  | 0 0 0 0 |
|   | 2 × 12,5 | 0 2 1 3 |
| II | 2 × 150 | 2 3 4 4 |
|   | 2 × 100 | 4 4 4 4 |
| III | 2 × 150 | 0 0 0 0 |
|   | 2 × 100 | 0 0 0 0 |
|   | 2 × 50  | 0 0 0 0 |
|   | 2 × 25  | 0 2 0 1 |
|   | 2 × 12,5 | 4 4 4 4 |
| infection controls | — — | 4 4 4 4 |

I = product of the invention: o-(2-diethylaminoethyl)-1-methyl-5-nitroimidazole-(2)-aldoxime monohydrochloride
II = comparative composition: 1-methyl-5-nitroimidazole-(2)-aldoxime
III = comparative composition: Metronidazol EXAMPLE 2: (test for activity)

Activity against *Entamoeba histolytica* was generally tested on cross-bred golden hamsters of both sexes. The body weight of each animal was generally in the range of from 50 to 60 g.

The substance to be tested was administered orally by means of an esophagal sound, either in an aqueous solution or, in the case of sparingly water-soluble compounds, in a Tylose suspension. The overall dosage was administered in four units, the first two hours prior to infection, the second two hours after infection, the third one day after infection and the fourth two days after infection. 4 Hamsters were used for each substance to be tested.

Infection was brought about by intrahepatic injection of 130,000 infective agents per animal as a suspension in 0.1 ml of TTY medium (*E. hist.-Crithidia culture*). The standard Metronidazol was administered by the

*same route and in the same dosage as the substance to be tested (see Table 2).*

As infection controls there were generally used 10 hamsters which were, after infection, not treated any more. Another 5 hamsters served as a zero control, that is to say, these animals were neither treated nor infected.

6 days at the earliest and eight days at the latest after infection, all the animals were killed. Subsequently, the state of the liver was judged according to the degree of icteric necrosis developed. Hamsters which had died during the period of infection were subjected to the same examination.

The observations on the state of the liver obtained with the tested composition and with the standard were compared with those of the infection controls. The scheme, according to which the liver findings (with tested composition and standard) were judged, was the following:

ineffective:

Icteric necrosis did not show any substantial difference from that of infection controls. Possible judgement: 3; 4 (in rare cases: 2).

effective:

a. faint: Icteric necrosis was less developed than with the infection controls. Possible judgement: frequently 2 (in rare cases: 1), b. unsatisfactory:

Icteric necrosis was substantially reduced as compared to infection controls. Possible judgement: 0 (in rare cases), predominantly 1;
(in rare cases: 2)

c. good: no icteric necrosis was discovered. Judgement: 0

TABLE 2

| composition | dosage in mg/kg golden hamsters, per os | liver findings Entamoeba histolytica (extraintestinal) in 4 golden hamsters |
|---|---|---|
| I | 4 × 150 | 0 0 0 0 |
|  | 4 × 100 | 0 0 0 0 |
|  | 4 × 50 | 0 0 0 0 |
|  | 4 × 25 | 0 3 0 1 |
| II | 4 × 150 | 0 0 0 0 |
|  | 4 × 100 | 1 0 0 0 |
|  | 4 × 50 | 3 0 2 0 |
|  | 4 × 25 | 1 4 2 0 |
| III | 4 × 150 | 0 0 0 0 |
|  | 4 × 100 | 0 0 0 0 |
|  | 4 × 50 | 0 1 0 2 |
|  | 4 × 25 | 3 0 2 0 |
| infection controls | — | 4 4 3 4 |

I = product of the invention: 0-(2-diethylaminoethyl)-1-methyl-5-nitroimidazole-(2)-aldoxime monohydrochloride
II = comparative composition: 1-methyl-5-nitroimidazole-(2)-aldoxime
III = comparative composition: Metroindazol.

Moreover, the product of the invention I has a superior activity in vitro against Trichomonas vaginalis up to 0.3 γ/ml, the comparative product II being active only up to 5 γ/ml and the comparative product III only up to 2.5 γ/ml.

Likewise, the product of the invention has a superior activity in vitro against Entamoeba histolytica up to 0.6 γ/ml, the compartive product II being active only up to 10 γ/ml and the comparative product III up to 5 γ/ml.

EXAMPLE 3: (preparation of active substances)

1. 0-(2-Diethylaminoethyl)-1-methyl-5-nitroimidazole-(2)-aldoxime monohydrochloride 2.3 g (0.1 mol) of metallic sodium were dissolved in small fractions in 100 ml of anhydrous methanol. That sodium-methylate solution was entirely evaporated in vacuo. A solution of 17.0 g (0.1 mol) of 1-methyl-5-nitroimidazole-(2)-aldoxime in 200 ml of dimethyl acetamide and then 13.6 g (0.1 mol) of diethylaminoethyl chloride were added to the residue and the reaction mixture was heated to 120°C for 1 hour in an oil bath. The solvent was entirely evaporated in vacuo and the residue was shaken with water and ethanol. The ether phase was dried over sodium sulfate, evaporated, the oily residue dissolved in 70 ml of abs. ethanol and the final product was separated in the form of hydrochloride by adding 4 N ethanolic hydrochloric acid.

19.5 g of 0-(2-diethylaminoethyl)-1-methyl-5-nitroimidazole-(2)-aldoxime monohydrochloride (64 % in the theory) were obtained in the form of yellow crystals which melted at 180°C.

The same compound was obtained by reacting equimolar amounts of 1-methyl-5-nitroimidazole-(2)-aldehyde and 0-(2-diethylaminoethyl)-hydroxyl amine in a solution of alcohol and water.

2. 0-(2-piperidinoethyl)-1-methyl-5-nitroimidazole-(2)-aldoxime monohydrochloride 4.65 g. (0.03 mol) of 1-methyl-5-nitroimidazole-(2)-aldehyde were dissolved in 50 ml of warm ethanol. After adding 6.52 g (0.03 mol) of 0-[2-piperidyl-(1)-ethyl]hydroxylamine-dihydrochloride in 15 ml of water the dropwise addition of a solution of 3.2 g (0.03 mol) of sodium carbonate in 15 ml of water was started. The mixture was then stirred at about 40°C for 4 hours, the ethanol was distilled off in vacuo, the mixture was diluted with water and the oxime was extracted with ethyl acetate. After drying over sodium sulfate and evaporating in vacuo the crude base precipitated from the extract in crystalline form (about 100 % of the theory). The hydrochloride was obtained by dissolving the base in dry ethyl acetate and adding dropwise 0.03 mol of ethanolic hydrochloric acid while stirring and thoroughly cooling. The product filtered off need not be further purified in general, but it may be done by recrystallization from ethanol.

7.3 g of 0-(2-piperidinoethyl)-1-methyl-5-nitroimidazole-(2)-aldoxime monohydrochloride (77 % of the theory) were so obtained which melted at 208–209°C (decomposition).

In an analogous manner, there may be obtained:

3. 0-(2-dimethylaminoethyl)-1-methyl-5-nitroimidazole-(2)-aldoxime monohydrochloride, melting point: 203°C;

4. 0-(2-pyrrolidinoethyl)-1-methyl-5-nitroimidazole-(2)-aldoxime monohydrochloride, melting point: 195°C;

5. 0-(2-morpholinoethyl)-1-methyl-5-nitroimidazole-(2)-aldoxime, melting point: 103°C;

6. 0-(2-N-methylpiperazinoethyl)-1-methyl-5-nitroimidazole(2)-aldoxime dihydrochloride, melting point: 215°C;

7. 0-(2-dimethylamino-1-propyl)-1-methyl-5-nitroimidazole(2)-aldoxime monohydrochloride, melting point: 197°C;

8. 0-(3-dimethylamino-1-propyl)-1-methyl-5-nitroimidazole(2)-aldoxime monohydrochloride, melting point: 215°C;

9. 0-(3-diethylamino-1-propyl)-1-methyl-5-nitroimidazole(2)-aldoxime monohydrochloride, melting point: 191°C;

10. 0-(3-pyrrolidine-1-propyl)-1-methyl-5-nitroimidazole-(2)-aldoxime monohydrochloride, melting point: 156°C;

11. 0-(3-piperidino-1-propyl)-1-methyl-5-nitroimidazole-(2)-aldoxime monohydrochloride, melting point: 174°C;

12. 0-(3-morpholino-1-propyl)-1-methyl-5-nitroimidazole-(2)-aldoxime monohydrochloride, melting point: 196°C;

13. 0-(3-N-methylpiperazino-1-propyl)-1-methyl-5-nitroimidazole-(2)-aldoxime dihydrochloride, melting point: 227°C.

14. 0-(2-diethylaminoethyl)-1-ethyl-5-nitroimidazole-(2)-aldoxime monohydrochloride, melting point: 170°C.

The compounds mentioned above can also be obtained by reacting equimolar amounts of 1-methyl-5-nitroimidazole-(2)-aldoxime with halogenated alkyl amines, as is described in example 1.

The 1-methyl-5-nitroimidazole-(2)-aldoxime used as starting substance was prepared in usual manner from the aldehyde or by reacting 1-methyl-2-chloromethyl-5-nitroimidazole with excess hydroxyl amine.

The 1-methyl-5-nitroimidazole-2-aldehyde used as starting substance was obtained by oxidation of the known 1-methyl-2-hydroxymethyl-5-nitroimidazole with manganese dioxide (cf. German Offenlegungsschrift No. 1,595,928).

The halogenated alkyl amines and the O-dialkylaminoalkylhydroxylamines are disclosed in German Offenlegungsschrift No. 1,470,317.

What is claimed is:

1. An 0-(substituted-aminoalkyl)-5-nitroimidazole-(2)-aldoxime of the formula

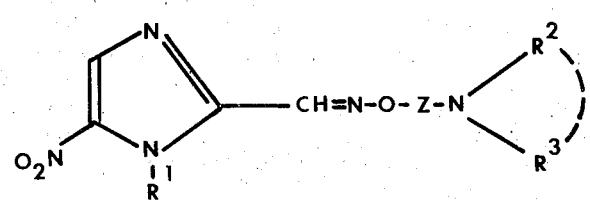

and non-toxic, physiologically-acceptable acid salts thereof, wherein $R^1$ is hydrogen, methyl, ethyl, or hydroxyethyl; Z is linear or branched alkylene having 2 to 3 carbon atoms; $R^2$ and $R^3$, taken alone, are the same or different lower alkyl having from 1 to 4 carbon atoms, and $R^2$ and $R^3$, taken together with the nitrogen atom to which they are attached, form a substituted or unsubstituted heterocyclic ring which may contain further hetero atoms.

2. A compound as in claim 1 wherein $R^2$ and $R^3$, taken together with the nitrogen atom to which they are attached, form a saturated heterocyclic ring selected from the group consisting of unsubstituted and methyl-substituted pyrrolidine, piperidine, morpholine, thiamorpholine, tetrahydro-1,4-thiazine-1,1-dioxide, and piperazine.

3. 0-(2-dimethylaminoethyl)-1-methyl-5-nitroimidazole-(2)-aldoxime monohydrochloride.

4. 0-(2-diethylaminoethyl)-1-methyl-5-nitroimidazole-(2)-aldoxime monohydrochloride.

5. 0-(2-pyrrolidinoethyl)-1-methyl-5-nitroimidazole-(2)-aldoxime monohydrochloride.

6. 0-(2-piperidinoethyl)-1-methyl-5-nitroimidazole-(2)-aldoxime monohydrochloride.

7. 0-(2-morpholinoethyl)-1-methyl-5-nitroimidazole-(2)-aldoxime monohydrochloride.

8. 0-(2-N-methylpiperazinoethyl)-1-methyl-5-nitroimidazole(2)-aldoxime dihydrochloride.

9. 0-(2-dimethylamino-1-propyl)-1-methyl-5-nitroimidazole-(2)-aldoxime monohydrochloride.

10. 0-(3-dimethylamino-1-propyl)-1-methyl-5-nitroimidazole-(2)-aldoxime monohydrochloride.

11. 0-(3-diethylamino-1-propyl)-1-methyl-5-nitroimidazole-(2)-aldoxime monohydrochloride.

12. 0-(3-pyrrolidino-1-propyl)-1-methyl-5-nitroimidazole-(2)-aldoxime monohydrochloride.

13. 0-(3-piperidino-1-propyl)-1-methyl-5-nitroimidazole-(2)-aldoxime monohydrochloride.

14. 0-(3-morpholino-1-propyl)-1-methyl-5-nitroimidazole-(2)-aldoxime monohydrochloride.

15. 0-(3-N-methylpiperazino-1-propyl)-1-methyl-5-nitroimidazole-(2)-aldoxime dihydrochloride.

* * * * *